US012564548B2

(12) United States Patent
Liu et al.

(10) Patent No.: US 12,564,548 B2
(45) Date of Patent: Mar. 3, 2026

(54) BAKE TYPE MAKEUP COSMETIC COMPOSITION AND METHOD FOR PRODUCING SAME

(71) Applicant: COSMAX, INC., Gyeonggi-do (KR)

(72) Inventors: Jing Yun Liu, Shanghai (CN); Tae Hee Kwon, Gyeonggi-do (KR); Youn Joon Kim, Seoul (KR)

(73) Assignee: COSMAX, INC., Gyeonggi-do (KR)

( * ) Notice: Subject to any disclaimer, the term of this patent is extended or adjusted under 35 U.S.C. 154(b) by 391 days.

(21) Appl. No.: 18/028,027

(22) PCT Filed: Feb. 25, 2021

(86) PCT No.: PCT/KR2021/002425
§ 371 (c)(1),
(2) Date: Mar. 23, 2023

(87) PCT Pub. No.: WO2022/102875
PCT Pub. Date: May 19, 2022

(65) Prior Publication Data
US 2023/0285265 A1     Sep. 14, 2023

(30) Foreign Application Priority Data

Nov. 16, 2020     (KR) ........................ 10-2020-0152738

(51) Int. Cl.
| *A61K 8/02* | (2006.01) |
| *A61K 8/73* | (2006.01) |
| *A61K 8/81* | (2006.01) |
| *A61K 8/84* | (2006.01) |
| *A61K 8/85* | (2006.01) |
| *A61Q 1/08* | (2006.01) |
| *A61Q 1/10* | (2006.01) |
| *A61Q 1/12* | (2006.01) |

(52) U.S. Cl.
CPC . *A61K 8/73* (2013.01); *A61K 8/84* (2013.01)

(58) Field of Classification Search
None
See application file for complete search history.

(56) References Cited

U.S. PATENT DOCUMENTS

2011/0293548 A1 *  12/2011  Caprarotta ............... A61Q 1/10
                                                          424/69

FOREIGN PATENT DOCUMENTS

| CN | 108366913 A | 8/2018 |
| CN | 111904871 A | 11/2020 |
| JP | S62-53914 A | 3/1987 |
| JP | 7002621-2 | 1/1995 |
| JP | 2011-251956 A | 12/2011 |
| KR | 10-2012-0091579 A | 8/2012 |
| KR | 10-2018-0053933 A | 5/2018 |
| KR | 10-2019-0007975 A | 1/2019 |
| KR | 10-1962337 B1 | 3/2019 |
| KR | 10-2020-0059990 A | 5/2020 |
| WO | WO-2020216138 A1 * | 10/2020 ............. A61K 8/731 |

OTHER PUBLICATIONS

International Search Report from corresponding PCT/KR2021/002425, dated Aug. 13, 2021.
First Office Action from corresponding Chinese Application No. 202110380645.2, Dated May 18, 2023.
Search Report from corresponding Chinese Application No. 202110380645.2, Dated May 18, 2023.
"Freeze-Drying Technology and Equipment" published by Huazhong University of Science and Technology Press, Wuchang, China (Zhao et al., eds, 2005), pp. 14-16, 199-200, and 205-207.
"Freeze-Drying Technology and Freeze Dryer" published by Chemical Industry Press, Beijing, China (Xu and Zheng eds., 2005), pp. 8-9.

* cited by examiner

*Primary Examiner* — Brian Gulledge
(74) *Attorney, Agent, or Firm* — Harness, Dickey & Pierce, P.L.C.

(57)     ABSTRACT

The present invention is a bake type cosmetic composition, and resolves issues of stability, shrinkage of content, loss of effective components, etc., which occur due to the conventional hot-air drying process, and is finer on a surface and enables the creation of various designs.

4 Claims, 2 Drawing Sheets

BAKE TYPE MAKEUP COSMETIC COMPOSITION AND METHOD FOR PRODUCING SAME

CROSS-REFERENCE TO RELATED APPLICATIONS

This application is a national phase application of PCT Application No. PCT/KR2021/002425, filed on 25 Feb. 2021, which claims priority to Korean Patent Application No. 10-2020-0152738, filed on 16 Nov. 2020. The entire disclosure of the applications identified in this paragraph is incorporated herein by reference.

TECHNICAL FIELD

The present invention relates to a bake type makeup cosmetic composition and a production method therefor.

BACKGROUND ART

In general, bake type makeup cosmetics such as a powder pact, eye shadow, and a blusher are manufactured through the processes of mixing a powder with oils to give a composition, loading the composition into a container, and then compressing same.

Recently, the creation of aesthetic effects on the appearance of these cosmetics has been widely achieved by such methods of forming three-dimensional patterns on the surface of cosmetics, wherein a powder, an emulsion, a volatile solvent, etc., are mixed to form a dough which is then molded by extrusion or melted and loaded into a mold.

The formation of patterns by removing volatile solvents in this way requires a drying process. On the whole, the drying process is conducted by drying with hot air at 40 to 80° C. for 4 to 12 hours. However, with the volatilization of a solvent during the drying process, the contents are likely to deform and shrink and thus undergo a change in stability and quality, which results in the loss of heat-labile components among the functional substances.

With respect to porous lyophilized patches and manufacturing methods therefor, reference may be made to Korean Patent No. 10-1962337 B that discloses a porous freeze-dried patch prepared with a porous mesh net and a manufacturing method therefor wherein the patch has excellent mechanical properties and flexibility.

DISCLOSURE OF INVENTION

Technical Problem

The present disclosure aims to prevent the loss of active ingredients due to hot-air drying during the production of a bake type makeup cosmetic composition and to implement a sophisticated surface pattern in cosmetics.

Solution to Problem

The present disclosure provides a method for producing a bake type cosmetic composition, the method including the steps of: (a) mixing a water-soluble gelling agent-containing aqueous phase part, an emulsifier, an oil phase part, and a powered part; (b) loading the mixture into a mold and cooling same; and (c) releasing the molded body from the mold and lyophilizing same after step (b).

In the present disclosure, the lyophilization in step (c) is carried out at a temperature of −60 to −20° C. under a pressure condition of 50 to 200 pa.

In the present disclosure, the water-soluble gelling agent is contained in an amount of 0.001-10% by weight, based on the total weight of the composition.

The water-soluble gelling agent used in the present disclosure is at least one selected from the group consisting of a polysaccharide, a synthetic polymer, and a derivative thereof. The polysaccharide includes at least one of gellan gum, xanthan gum, agar, carrageenan, and algin. In addition, the synthetic polymer includes a polyester, a polyacrylate, and a polymethacrylate.

In the present disclosure, the lyophilization in step (b) may be carried out at −60 to −20° C.

Also, the present disclosure provides a bake type cosmetic composition produced by the method.

The bake type cosmetic composition of the present disclosure may include 30 to 60% by weight of an aqueous phase part, 1 to 5% by weight of an oil phase part, 0.1 to 3% by weight of an emulsifier, and 20 to 60% by weight of a powder part.

Advantageous Effects of Invention

Characterized by including a lyophilization process, the method for producing a bake type cosmetic composition according to the present invention solves the problems, caused by conventional hot-air drying processes, including shrinkage, loss, and instability of active ingredients and allows for the formation of finer and more diverse designs on the cosmetic surface.

BEST MODE FOR CARRYING OUT THE INVENTION

Figure 1:
FIG. 1 is a photographic image of the appearance of a solid-phase cosmetic material prepared according to an Example of the present disclosure.

Hereinafter, the present disclosure will be described in detail with reference to the accompanying technology so that those of ordinary skill in the art can easily implement the present disclosure. However, it will be apparent to those skilled in the art that the present disclosure may be implemented in various forms and is not limited to the embodiments described herein.

The present disclosure pertains to a method for producing a bake type cosmetic composition, the method including the steps of: (a) mixing an aqueous phase part, a water-soluble gelling agent, an emulsifier, an oil phase part, and a powered part; (b) loading the mixture into a mold and cooling the mixture; and (c) releasing the molded body from the mold and lyophilizing same after step (b).

According to the present disclosure, the problems, caused by conventional drying with hot air, including shrinkage and deformation of contents, decreased formulation stability, and loss of effective components, can be solved. As used herein, the term "effective components" refers to heat-labile functional components as exemplified by vitamin C, plant extracts, etc.

The lyophilizing process of the present disclosure is carried out at a temperature of −60 to −20° C. under a pressure condition of 50 to 200 pa. Taking advantage of the phenomenon that water contained in a formulation freezes and then sublimates blow the triple point, the lyophilization can prevent the quality deterioration caused by conventional drying processes such as hot-air drying, etc. In detail, lyophilization is initiated by putting a cosmetic material into a freeze drier maintained at the same temperature as in step (b) of conducting a cooling process, decompressing the freeze drier to a reduced pressure, and maintaining the freeze drier in a vacuum state. The ice is sublimated at such a low pressure to generate water vapor that, in turn, increases the internal pressure. The pressure in the freeze drier is again reduced into 50 to 200 Pa and maintained thereat to conduct lyophilization.

In the method for production of a bake type cosmetic composition according to the present disclosure, first, step (a) of mixing an aqueous phase part, a water-soluble gelling agent, an emulsifier, an oil phase part, and a powered part is carried out. In greater detail, an oil phase part is added to an aqueous phase part containing a water-soluble gelling agent and an emulsifier to form an emulsion. A cosmetic material in a powdered state is then added to the emulsion, homogeneously mixed, and melted by heating. The aqueous phase part may further contain purified water, a moisturizer, etc.

Step (a) may be carried out by mixing a water-soluble gelling agent, an emulsifier, and purified water to form an aqueous phase part, mixing the aqueous phase part with an oil phase part to form an emulsion, and homogeneously mixing a powered part with the emulsion by stirring, etc.

The emulsifier used in step (a) is added to the aqueous phase part and preferably used in an amount of 0.1-3% by weight based on the total weight of the composition. When the emulsifier is used at a content higher than 3% by weight, there is only an insignificant increment of emulsification.

The gelling agent used in step (a) is preferably a water-soluble gelling agent that can be dissolved or dispersed in an aqueous phase to stabilize the aqueous phase. The water-soluble gelling agent melts at a high temperature (e.g., 80° C. or higher) or dissolves in water to maintain a liquid state, and when cooled to a low temperature (e.g., 10° C. or lower), the water-soluble gelling agent gels and becomes a solid state.

So long as it is available in cosmetics, any water-soluble gelling agent can be used. The gelling agent is preferably selected from the group consisting of polysaccharides, synthetic polymers, and derivatives thereof, but with no limitations thereto.

Specifically, the water-soluble gelling agent may be a polysaccharide selected from the group consisting of gellan gum, xanthan gum, agar, carrageenan, algin, and derivatives thereof.

A synthetic polymer available as the gelling agent may include at least one of polyesters, polyacrylates, polymethacrylates, and derivatives thereof.

The water-soluble gelling agent is preferably used at a content of 0.001-10% by weight based on the total weight of the bake type cosmetic. In order to stabilize the aqueous phase, the water-soluble gelling agent may be contained in an amount of 1% by weight or greater and more preferably in an amount of 2-5% by weight. When the content of the water-soluble gelling agent exceeds 10% by weight, the bulk is difficult to load into a mold due to the high viscosity thereof.

So long as it is typically used in a cosmetic material, any oil may be contained in the oil phase part in step (a) without limitations, as exemplified by ester-based oils, hydrocarbon-based oils, silicon oils, etc.

The ester-based oils may include at least one selected from the group consisting of caprylic/capric glyceride, cetyl ethylhexanoate, isocetyl ethylhexanoate, isocetyl myristate, isopropyl myristate, neopentyl glycol dicaprate, hexyl laurate, triethylhexanoin, pentaerythrityl tetraoctanoate, ethylhexyl palmitate, and isononyl isononanoate, but with no limitations thereto.

The hydrocarbon-based oils may include: synthetic oils such as hydrogenated polydecene, synthetic squalene, polybutene, etc.; and vegetable oils such as vegetable squalene, hydrogenated squalene, etc., but are not limited thereto. Examples of the hydrocarbon-based oils include octyldodecanol, hydrogenated polydecene, hydrogenated polyisobutene, squalane (vegetable squalane), and synthetic squalane, but are not limited thereto.

In addition, the powder contained in the powdered part in step (a) may include at least one selected from the group consisting of talc, mica, sericite, globular silica, plastic powder, titanium dioxide, nacreous pigments (pearl), and boron nitride. Furthermore, coated pigments may be employed, but with no limitations thereto.

Purified water contained in the aqueous phase part may be substituted with an extract from plants.

Moreover, the aqueous phase part of the present disclosure may further include a moisturizer. The moisturizer may be at least one selected from the group consisting of 1,3-butylene glycol, glycerin, diglycerin, propylene glycol, dipropylene glycol, pentylene glycol, propanediol, and hyaluronic acid.

The melting temperature in step (a) is a temperature at which the gelling agent is melted to maintain the gelling agent-containing cosmetic composition in a liquid state and the mixed composition retains fluidity and thus is easy to load into a mold. Preferably, the melting temperature is 40 to 90° C.

In the method for producing a bake type cosmetic composition according to the present disclosure, step (b) of loading the mixture prepared through step (a) into a mold and cooling same is carried out. In this regard, the mold may be made of any material that can be designed, such as silicon, rubber, or metal.

When the cooling process is performed on the cosmetic material loaded into the mold, the cosmetic material is gelled at a low temperature due to the water-soluble gelling agent, so that the cosmetic material can be manufactured according to the mold design. Even when released from the mold thereafter, the cosmetic material can retain the shape and surface design.

The cooling process is preferably performed at −20 to −60° C., more preferably at −40° C. or less. At higher than −4° C., cooling does not work well. At −4° C. to −20° C., water in a non-pearl type mixture freezes to form many crystals which have an undesirable effect. At a temperature lower than −60° C., the effect of the cooling temperature is insignificant and safety problems such as frostbite risk for workers may occur. Thus, the cooling process may be preferably carried out at −40° C. or less.

The present disclosure is also drawn to a bake type cosmetic composition produced by the method.

In the present disclosure, the cosmetic material is prepared by mixing an aqueous phase part, an oil phase part, an emulsifier, and a powered part. In detail, the composition may contain 30 to 60% by weight of an aqueous phase part, 1 to 5% by weight of an oil phase part, 0.1 to 3% by weight of an emulsifier, and 20 to 60% by weight of a powered part, based on the total weight thereof.

In the cosmetic composition of the present disclosure, the aqueous phase part may contain a water-soluble gelling agent and an emulsifier. So long as it is available for a cosmetic material, any water-soluble gelling agent can be employed. The gelling agent is preferably selected from the group consisting of a polysaccharide, a synthetic polymer, and a derivative thereof, but with no limitations thereto.

Specifically, a polysaccharide accounting for the water-soluble gelling agent may be selected from the group consisting of gellan gum, xanthan gum, agar, carrageenan, algin, and derivatives thereof.

A synthetic polymer available as the gelling agent may include at least one of polyesters, polyacrylates, polymethacrylates, and derivatives thereof.

From the standpoint of those skilled in the art, the cosmetic composition of the present invention may further include any additional component and/or amount thereof selected and added as long as it does not affect the advantageous properties of the composition. For example, the composition may further contain any conventional cosmetic ingredient selected from colorants, fragrances, fillers, preservatives, preservatives, neutralizers, sunscreens, sweeteners, vitamins, sequestering agents, and mixtures thereof. In addition, contents thereof can also be adjusted within the range commonly used.

Hereinafter, the present disclosure will be described in detail with reference to Examples and Experimental Examples. However, the Examples and Experimental Examples according to the present disclosure can be modified into various other forms, and the scope of the present disclosure should not be construed as being limited to the Examples and Experimental Examples. The Examples and Experimental Examples of the present disclosure are provided to more completely explain the present disclosure to those of ordinary skill in the art.

EXAMPLES

1. Preparation of Solid-Phase Cosmetic Composition (1) Example 1: Preparation of Solid-Phase Cosmetic Composition A solid-phase cosmetic composition of Example 1 was prepared as shown in Table 1 (unless stated otherwise herein, the content unit of ingredients is % by weight).

Individual ingredients are weighed according to the contents thereof (% by weight) as shown in Table 1. The aqueous phase part and the water-soluble gelling agent were mixed and dispersed at 75° C. and then emulsified while the oil phase part was slowly added thereto. Afterward, the emulsion was homogenously mixed with the powered part, after which the homogenous mixture was heated to up to 95° C., spontaneously degassed, and cooled to 30° C. to prepare a cosmetic material.

The cosmetic material was then melted and loaded as a slurry into a designed silicon mold. After the cosmetic material in the mold was quenched to −30° C., the cosmetic material was released from the mold. The released cosmetic material was put into a freeze drier maintained at the same temperature (−30° C.) and lyophilized at a reduced pressure. As lyophilization proceeded, the pressure changed due to the sublimation of moisture in the cosmetic material. Thus, adjustment was made to maintain a pressure of 50-200 pa during the lyophilization process. Through this lyophilization process, a demoisturized, solid-phase cosmetic material was prepared.

TABLE 1

| Class | Ingredient | Content (% by wt) |
|---|---|---|
| Aqueous phase part | purified water | To 100 |
| | Moisturizer (Glycerin) | 0.1~5 |
| | Emulsifier (POLYSORBATE 80, C12-20 Acid PEG-8 Ester) | 0.1~1.0 |
| Gelling agent | Xanthan gum, Carrageenan | 0.001~10 |
| Oil phase part | Octyldodecyl stearoyl stearate, squalane | 0.1~5 |
| Powered part | MICA, CI 77891 CI 77491, CI 75470, SILICA, CETEARYL ETHYLHEXANOATE (oil binder) | 20~60 |

(2) Comparative Examples: Preparation of Solid-Phase Cosmetic Composition

After being prepared, the cosmetic material having the composition shown in Table 1 was pressed in a slurry state by a metal punch, as in general pressed powder, to form a surface pattern and then dried (Comparative Example 1). In addition, the cosmetic material in a slurry state was loaded into a silicon mold and dried with hot air (Comparative Example 2).

(3) Observation with Naked Eye

The appearances of the solid cosmetic materials prepared according to the Examples of the present invention were observed. With reference to FIG. 1, it was observed with the naked eye that the cosmetic composition prepared through a lyophilization process according to the present disclosure (lyophilization method) was less apt to shrink and deform and had fine and neat patterns formed on the surface thereof, compared to those in the Comparative Examples.

Figure 2A:
FIGS. 2A and 2B are photographic images of the appearance of a solid-phase cosmetic material prepared according to Comparative Examples.
Figure 2B:
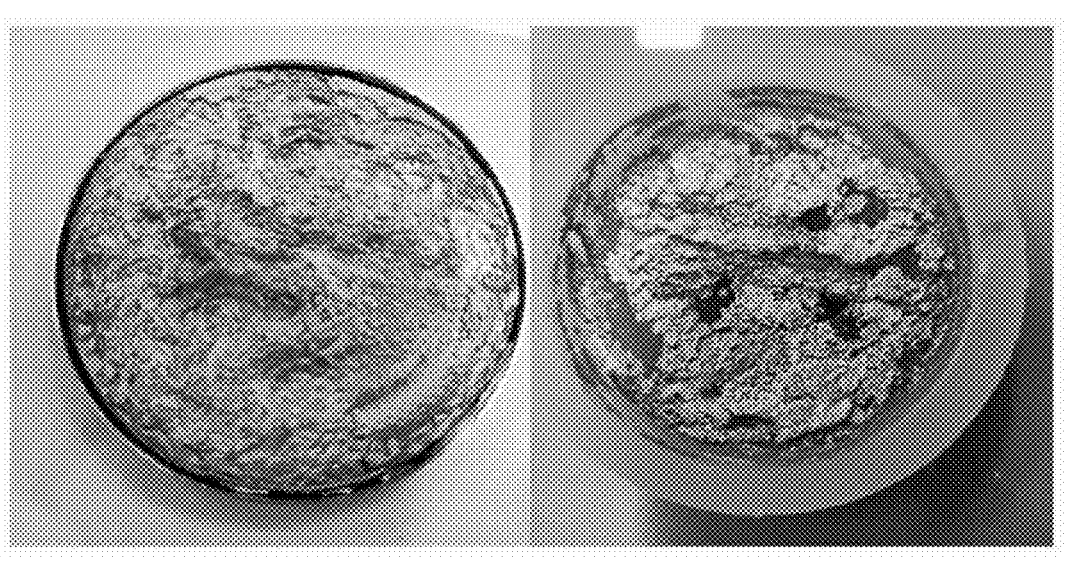

However, referring to FIGS. 2A and 2B, the composition of the Comparative Example 1 was poor in terms of elaboration (FIG. 2A) and the composition of the Comparative Example 2 was difficult to provide with a surface pattern and neatly release from a mold (FIG. 2B).

What is claimed is:

1. A method for producing a bake type cosmetic composition, the method comprising the steps of:

(a) mixing a water-soluble gelling agent-containing aqueous phase part, an emulsifier, an oil phase part, and a powered part;

(b) loading the mixture into a mold and cooling the mixture; and (c) releasing the molded body from the mold and lyophilizing same after step (b), wherein the cooling in step (b) is carried out at a temperature of −60 to −30° C., wherein the lyophilizing in step (c) is carried out at a temperature of −60 to −30° C., under a pressure condition of 50 to 200 pa, wherein the bake type cosmetic composition includes 30 to 60% by weight of an aqueous phase part, 1 to 5% by weight of an oil phase part, 0.1 to 3% by weight of an emulsifier, and 20 to 60% by weight of a powder part, based on the total weight of the composition, wherein the water-soluble gelling agent is contained in an amount of 0.001-10% by weight, based on the total weight of the composition.

2. The method of claim 1, wherein the water-soluble gelling agent used in the present disclosure is at least one selected from the group consisting of a polysaccharide, a synthetic polymer, and a derivative thereof.

3. The method of claim 2, wherein the polysaccharide comprises at least one of gellan gum, xanthan gum, agar, carrageenan, and algin.

4. The method of claim 2, wherein the synthetic polymer comprises a polyester, a polyacrylate, and a polymethacrylate.

* * * * *